United States Patent [19]

Komarniski

[11] 4,027,979
[45] June 7, 1977

[54] MULTIPLE CHEMISTRY ANALYZER

[76] Inventor: John Victor Komarniski, 2167 Burr Court, Santa Cruz, Calif. 95062

[22] Filed: Apr. 27, 1973

[21] Appl. No.: 355,171

[52] U.S. Cl. .............................. 356/180; 73/425.6; 250/227; 250/573; 356/184; 356/201
[51] Int. Cl.$^2$ ......................................... G01J 3/46
[58] Field of Search .......... 356/180, 184, 208, 201; 250/227, 573, 574

[56] References Cited

UNITED STATES PATENTS

| | | | |
|---|---|---|---|
| 2,324,304 | 7/1943 | Katzman | 356/208 |
| 2,725,782 | 12/1955 | Worley | 356/208 |
| 3,164,663 | 1/1965 | Gale | 250/227 |
| 3,705,773 | 12/1972 | Vicario | 356/180 |
| 3,727,066 | 4/1973 | Louderback et al. | 356/201 |

Primary Examiner—Vincent P. McGraw

[57] ABSTRACT

The multiple chemical analyzer incorporates an improved multiple diluter, multiple pipettor, multiple colorimeter with probes and a signal storage device into a machine whereby a number of samples are tested and a signal of the colorimetric value of each sample is obtained simultaneously. Agitation, time and temperature can be selected. The record on film or in electronic storage units can be supplied to a computer or interpreted individually by a voltage measurement of the stored signal or if recorded on photosensitive material like film, the densities are measured or visually compared with standards. With the multiple chemical analyzer the operator can perform a single analysis on many test samples or a number of analysis on one or more test samples simultaneously. Multiple dilutors and a portable probe colorimeter like a photographic light meter and a variety of colorimeter probes are described.

3 Claims, 9 Drawing Figures

VARIATION OF MULTIPLE PROBE COLORMETER

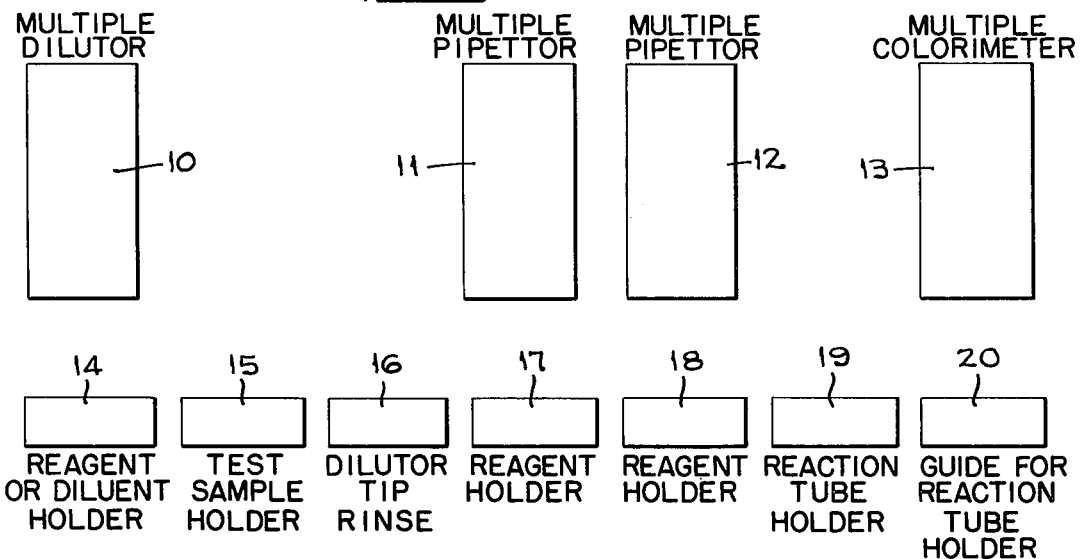
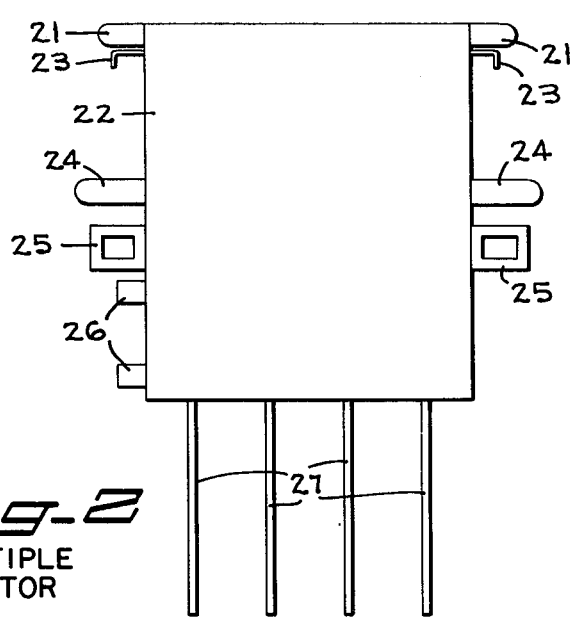
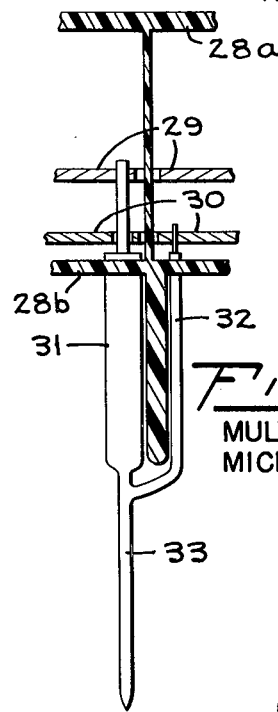
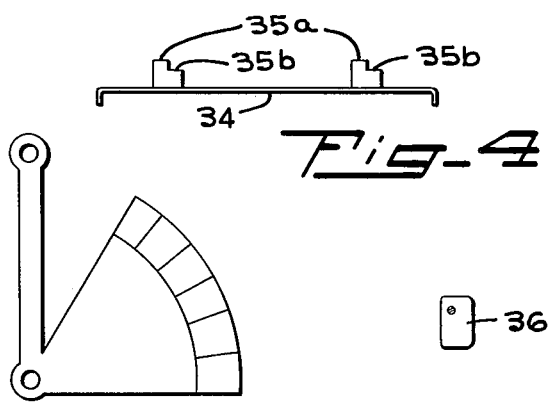
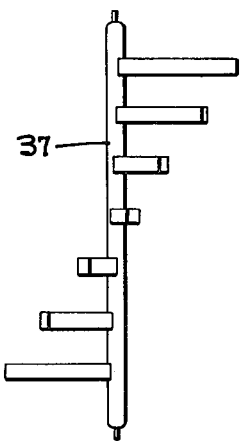

38
39
40
41
42
TEST SAMPLE HOLDER
TEST SAMPLE HOLDER BASE 44  43

REACTION TUBE HOLDED 48, 49, 45, 46, 47
PORTABLE PROBE COLORIMETER
51, 50, 52, 53, 54

FILM HOLDER AND PROBES

MULTIPLE CHEMISTRY ANALYZER

SUMMARY OF THE INVENTION

Testing in the clinical laboratory has been multiplied in recent years to the extent of a multiple of tests on a multiple of patients and the need for multiple testing is evident. The purpose of this invention is to increase the volume and reduce the cost of testing. The reagents and methods are easily adapted and use is flexible. In performing a number of tests the tubes containing the samples are placed in the test sample holder which holds the test samples, controls, and standards in a row or rows in a pattern congruent with the pattern of the dilutors, pipettors, reaction tubes in the reaction tube holder, and the colorimeter probes. An operator performs many tests about a quickly as a single test by handling many test samples and reagents simultaneously.

A single colorimeter probe has been mounted to a modified photographic light meter and found useful in making a series of colorimetric determinations quickly and without handling the samples but by inserting the probe into each sample and reading the values.

BRIEF DESCRIPTION OF THE DRAWINGS

In the drawings forming part of this application:

FIG. 1 is the flow chart. The multiple dilutors, multiple pipettors, and the multiple probe colorimeters have their sampling or testing projections all in the same pattern to interchangeably enter the tubes in the test sample holders, the reagent holders and the reaction tube holders.

FIG. 2 is a multiple dilutor incased for circulation of cooling or heating liquid for diluting wherein the temperature control is critical.

FIG. 3 shows a multiple micro dilutor that is constructed like two multiple pipettors with common tips for each two pairs of cylinder and plunger combinations. The drawing is an end view of a single row.

FIG. 4 illustrates stops of various types designed to control the amount of the diluent and/or air bubble, and sample to be metered by the multiple dilutor, or a variety or a number of dispensings to be metered by the multiple pipettor.

DESCRIPTION OF THE PREFERRED EMBODIMENTS

Figure 5:
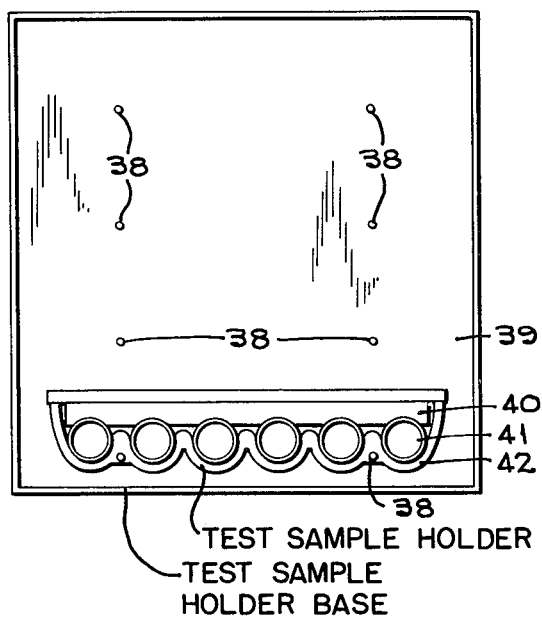
FIG. 5 is a top view of a test sample holder base and one test sample holder section in place.
Figure 6:
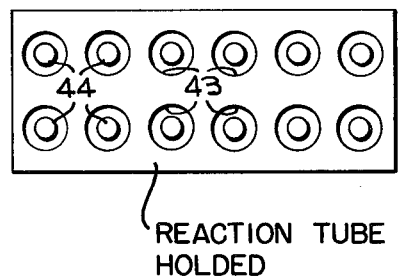
FIG. 6 is a top view of a reaction tube holder with a photoelectric element in the bottom of each opening. The usual reaction tube holder is constructed for temperature control even at different temperatures for different reaction tubes as needed, and agitation. The reaction tubes may be constructed as part of the reaction tube holder or removable. A cover may be used.

Tests are performed simultaneously by placing the tubes 41 with the samples to be tested, controls and standards in a row or rows in a test sample holder FIG. 5 and aligning the surface of each liquid in each tube 41 to be the same height guided by a horizontal line or some indicator. A sponge 40 or means to cause friction in the holes holds the test sample tube 41 at any height. Pins 38 align and hold additional rows. Some test tube racks may be used as test sample holders. The reagents as needed are poured into the reagent holers 14, 17, 18 which may have "V" grooves or depressions for the multiple dilutor tips 27. The edge of the reagent holder is thin to allow the dilutor tips 27 and pipettor tips (not shown) to be used with some of the tips 27 outside of the reagent holder when the number of the tests performed is less than the number of dilutor tips 27. The reagent or diluent flows into reservoirs (not shown) above each tip 27 when the tips 27 are inserted into the reagent or diluent holder and the handles 24 are pressed to the handles 21. The amount of fluid is controled by the dilution selector 23 chosen and inserted between the moveable handles 24 and the upper stationary handles 21. A variety of dilution selectors and stops shown in FIG. 4 including hydraulic and screw types not shown are useful in multiple dilutors and multiple pipettors to control the dilutions and the amounts of liquid metered. If the dilution selector 23 is like the dilution selector 34 in FIG. 4 the stops 35a are moved slightly to the side aligning stops 35b with the projections from either handles 21 or handles 24. The tips 27 are removed from the fluid in the reagent or diluent holder 14 and usually dried. The handles 24 are pressed to the handles 21 again drawing an air bubble into each tip 27. The air bubble step may be omitted but is has the advantage of separating the reagent or diluent from the sample to be drawn which may otherwise diffuse into the reservoir thus contaminating the dilutor. The dilution selector 23 is moved to align the base 34 FIG. 4 with the projections from the handles with which the stop 35b was previously aligned and used for the air bubble. The dilutor tips 27 are inserted into the test samples, controls and standards in the test sample holder 15 also FIG. 5, and the handles 24 are pressed to handles 21. Now a measured aliquot of each sample has been drawn into each tip and the tips are usually rinsed. The tips 27 are positioned over the reaction tubes in the reaction tube holder 19 and the handles 24 are pressed to the lower stationary handles 25 which expells the samples from the tips 27 first and the reagent or diluent follows removing the rest of the sample from each tip 27. Additional reagents as are needed are pipetted into the reaction tubes with the multiple pipettors 11, 12 from the reagent holders 17, 18.

At the end of the reaction time the reaction tube holder 19 is aligned by the guide 20 or the multiple colorimeter is positioned over the reaction tube holder so that each colorimeter probe 50 through 54 enters a reacted test, control or standard sample. The colorimeter probe lights 54 are turned on, and then the function switch is turned to "expose" position and timed for the "exposure". During the "exposure" the light 54 of each colorimeter probe is on and focused by lens 53 through the liquid being tested in space 52 and into the light transporting medium 51 from where it is passed through the monochromatic filter 47 and strikes the photoelectric element 46 where it causes a change of electrical current and voltage which is effected by the amount of light absorbed by the sample in the space 52. The current from each photoelectric element 46 charges one signal storage device usually a capacitor when the function switch is in the "expose" position and at the end of the "exposure" time usually ten seconds or less the function switch is turned to "read" position. In the "read" position the photoelectric elements 46 are electrically disconnectd from the signal storage device but each signal storge device is electrically connected to its own position on the selector switch which has also a neutral position. When the operator is ready to compare the reactions colorimetrically he turns the selector switch to a reaction tube number which connects that corresponding signal storage device to the meter, recorder or computer. The multiple colorimeter 13 has as many colorimeter probes 46, 47, and 50 through 54 as reaction tubes in the reaction tube holder 19 for simultaneous testing. If the type of test is such that the reaction color is stable a reduced number of colorimeter probes may be used repeatedly to obtain a record from each test sample by electrically switching each time to a signal storage device corresponding to the test samples tested, or the portable probe colorimeter FIG. 7 or a single probe colorimeter (not shown) may be used.

Figure 7:
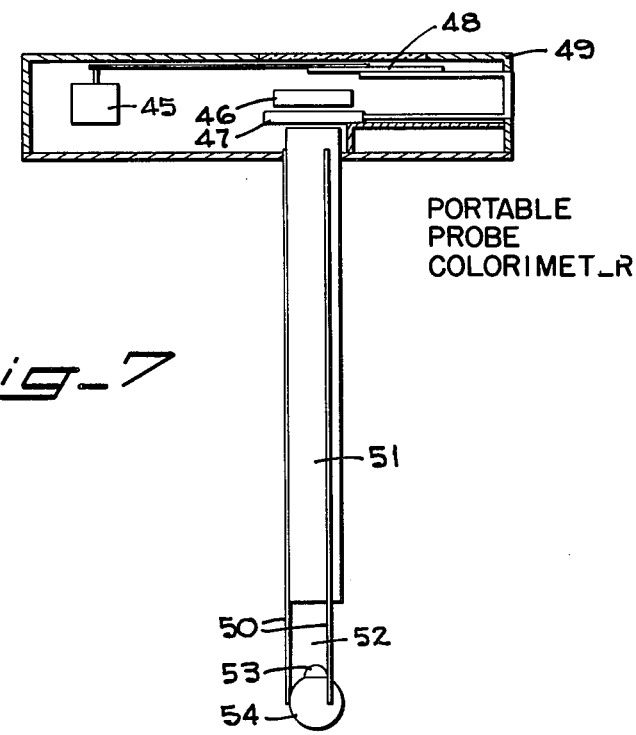
FIG. 7 is a portable probe colorimeter.

The portable probe colorimeter FIG. 7 is easily held in one hand and the switch (not shown) is pressed while the probe is dipped in the liquids for comparing their color or turbidity. The meter 45 has a quick response and twenty tests can be compared in about a minute. When the switch is pressed the light 54 is on and the electronic circuit controled by the photoelectric element 46 is activating the meter 45 and the meter pointer indicates the test value on the scale 48 in the units wherein the test is normally reported. The scale 48 and the filter 46 slide out of the case 49 and are exchanged when needed for a different chemical test. A few filters 46 mounted on a wheel or a strip in case 49 in a manner that a filter of the desired wavelength is pushed or turned into position is satisfactory. The probe is usually coated or constructed with chemical resistant and wet resistant material. The part of the probe that is dipped into the liquid while testing is the lower end of the light transporting medium 51 which usually has an opaque coating on its entire wall, the electrical conductors 50 which also can support the light 54, and the light 54 with its lenses 53. Space 52 about one centimeter long fills with the reaction liquid and absorbs light from the light 54 usually in direct proportion to the units, grams, or milligrams per deciliter of the chemical in the test sample. The advantage of having a removable scale is that scales can be prepared for the tests that do not follow the direct proportion rule using a series of knowns.

Another embodiment is the single probe colorimeter not shown but similar to the portable probe colorimeter FIG. 7. The meter 45, scale 48, and the case 49 with the electronics are much larger and are connected electrically by a length of flexible electrical conductors, two feet are satisfactory, to the colorimeter probe 50 through 54 with its photoelectric element 46 and filter 47. The large scale offers better reading accuracy, or a digital meter or computer may be used.

In FIG. 7 is a colorimeter probe that is a preferred embodiment for use in multiple. Variable resistors in series with each light 54 may be used to standardize all the colorimeter probes with a standard solution. Other means of adjusting for standardizing each colorimeter probe are diaphrams, filter, and density films with increasing density placed in the light path, and then there are electronic methods with variable resistors and amplifiers. Some of the variations in the construction of the colorimeter probe are to place the light source and/or filter and lens above the space 52 FIG. 7 and the photoelectric element and/or the filter and lens below the space 52. The space 52 wherein the liquid enters for colorimetric comparison may be a fraction of a centimeter or several centimeters long and does not need to be on a vertical plane. The photoelectric element and filter and the light source with its lens and/or filter have been constructed on the opposite sides of the tube for sample testing. The light transporting medium 51 FIG. 7 has been replaced by a rod by placing the photoelectric element and/or the filter on the end that is dipped into the liquid. The use of light transporting medium offers the advantage of placing the light source, or filters, and/or photoelectric elements or photosensitive materials out of the liquid that is for color or turbidity testing and in a convenient place.

Figure 8:
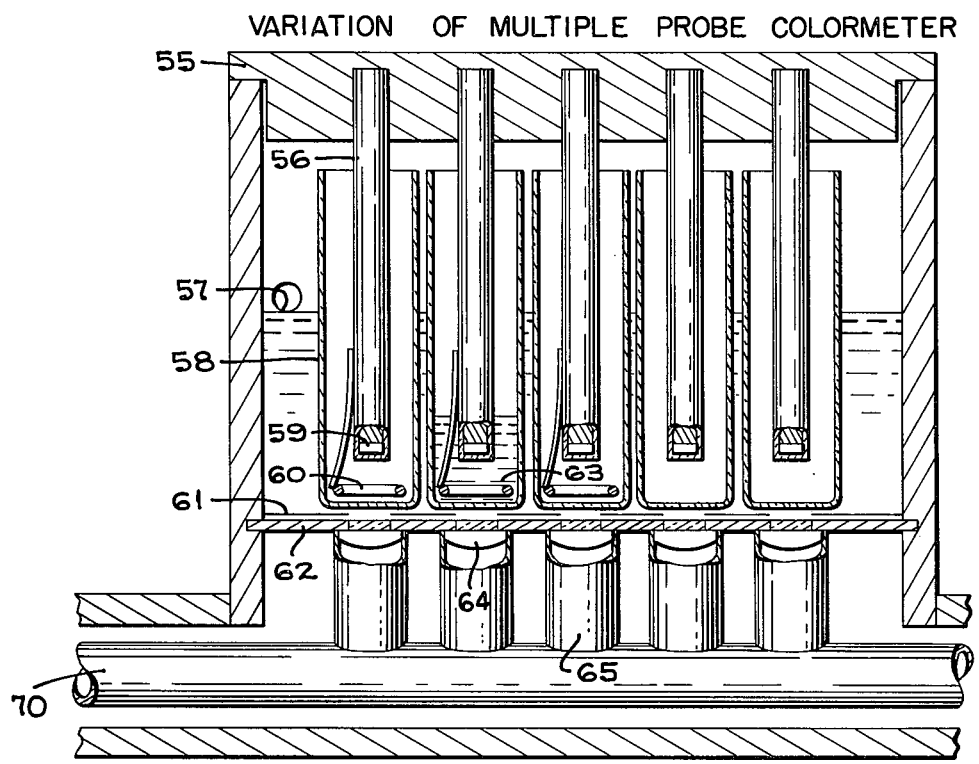
FIG. 8 is a combination of a reaction tube holder and a variation of the multiple probe colorimeter in a light tight chamber with the colorimeter probes mounted n the removable cover.

The combination in FIG. 8 has some advantages. The light source 70 is a large diffused ultra-violet light with opaque hollow tubes 65 directing the light into the bottom of flat bottom reaction tubes 58 through a lens 64 focusing the light into the ends of the flat bottom glass tubes 56 that contain photoelectric elements 59. The lens 64 is attached to a second bottom 62 which holds the circulating liquid, second bottom 62 is overlayed with apertured opaque shield 61. There is one centimeter space between the inside bottom of the flat reaction tube 58 and the flat bottom of the tube 56. The walls are opaque of the tubes 58 and the probes 56, but the flat bottoms which can be a lens instead are transparent. A plastic stirrer 60 projects near the bottom of the reaction tube 58 in the shape of a ring and is useful to stir the samples 63 during the reaction time when enzyme tests are made. Strict temperature control is possible because of the liquid circulating through the multiple dilutor FIG. 2, inlet and outlet 26, and circulating liquid at the proper temperature through the light tight chamber FIG. 8. The inlet is not shown but the water level can be up to the outlet 57. Raising and lowering the cover 55 stirs all of the samples simultaneously. When a colorimeter probe type in FIG. 7 is used the stirrer ring 60 is omitted because the colorimeter probe with the light 54 on its end makes a good stirrer.

Five sets of signal storage devices have been included for rate of reaction studies. Five signal storage devices for each photoelectric element 59 and a second selector switch with six positions selects a set of five signal storage devices at each position except the sixth position which is neutral. Therefore simultaneous recordings of a set of tests may be repeated in different sets of signal storage devices a few seconds apart and compared later to demonstrate the progressive changes of each reaction 63 for each time interval. Although FIG. 8 shows only one liquid reaction 63 five reaction tubes 58 each contain a liquid reaction 63.

Figure 9:
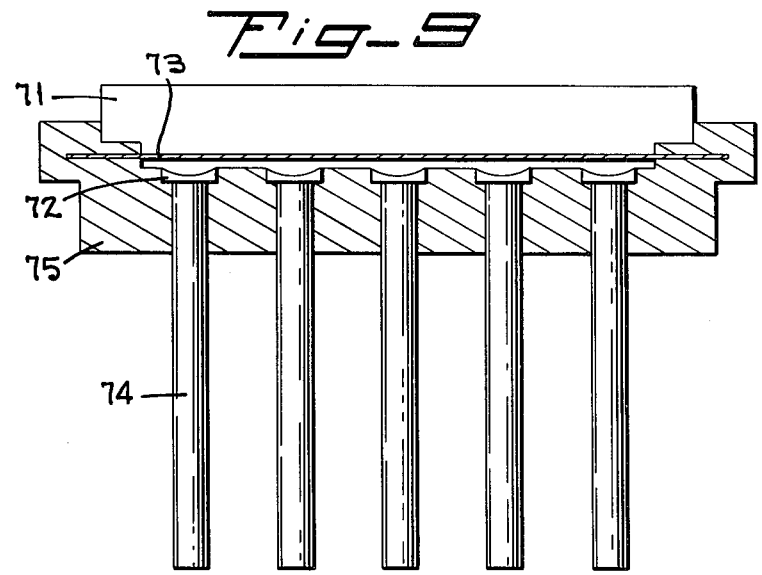
FIG. 9 is another cover for the light tight reaction chamber in FIG. 8.

Another embodiment is FIG. 9 which allows a record on film of rate of reaction studies by placing the film adapter unit FIG. 9 on the chamber of FIG. 8 in place of the cover 55 as shown. Using a high contrast photosensitive material the change in density can be followed. The probes 74 are inserted into the reactions 63 and transport the light 70 through the lenses 72 and to the film in the film holder 71 when the shutter 73 is open. The opening and closing of the shutter 73 once makes a record of each of the five reactions 63 simultaneously. At timed intervals the film holder 71 or the photosensitive material is moved about threefourths inch and the shutter 73 is opened, accurately timed and closed. Thus simultaneous records may be repeated eight times on a five by seven inch photographic printing paper to demonstrate the progress of each of the five reactions 63. A comparison of the density or size of the corresponding spots with standards indicates the amount of reactions 63. Photosensitive material in rolls or Polaroid type are useful.

Also records of certain chemical characteristics of liquid samples may be made by arranging the light source or sources and/or filters near the top of the light tight chamber with the light trasmporting medium carrying the light from the light source downward and into the surface of inch liquid sample contained in tubes with optical bottoms and the light being focused through a desired distance of each sample, through the optical bottom of each tube, through a monochromatic filter if desired and onto a medium to record the light intensity. The medium to record the light intensity may be photoelectric elements used as previously described herein or a photosensitive material to record the light not absorbed by the liquid samples using a timed exposure with a light switch or a shutter.

The multiple micro dilutor FIG. 3 transfers or dilutes micro samples in multiple. These units FIG. 3 are constructed in rows and all of the plungers operating in the larger cylinders 31 are attached to a handle 29 whereby all of the plungers in the larger cylinders are operated in unison and the amount of liquid drawn through the tips 33 and into the cylinders 31 is controlled by any stops FIG. 4 including screw and hydraulic types not shown. Usually four stops are mounted near the corners of the multiple micro dilutor between the upper handle 28a and the lower handle 28b which are stationary. A knob (not shown) adjusts all four stops in unison to select the distance that the movable handle 29 may be pressed to the upper stationary handle 28a. If stops like stop 37 FIG. 4 are used mounted vertically then the dilution selector knob would align a pin projecting from each stop 37 in a manner to stop the movable handle 29 as it is pressed to the upper stationary handle 28a. Also a second pin would be in in alignment and projecting from stops 37 in position to stop the second movable handle 30 which operates the smaller set of plungers in the cylinders 32. A choice of the amount of the diluent and sample ratios are available with the dilution selector knob (not shown). A combination of stops may be employed if desired. For example a large shim has been constructed to it slides like stop 23 FIG. 2 either with openings or projections that align between the place of contact of the handle 29 and the pins projecting from the stops 37 in a manner that when the shim is moved the movable handle 29 may be pressed to the upper stationary handle 28a and the distance is such that a small air bubble is taken into into the tips 33. All of the plunger and cylinder combinations mentioned herein have an airtight seal at the bottom end of the plunger, or at the top of the cylinder, or throughout the length of the plunger and cylinder, or a combination of seals.

Although specific reactions, numbers of units, construction materials and arrangements are presented in the descriptions or drawings herein to illustrate more easily the principles of the invention, the intention of the invention is not to specify reactions, numbers, materials, distances, size, or specific arrangements. It will be obvious to those skilled in the art that many variations can be made in the exact structure shown without departing from the spirit of this invention. The term "light" is used herein but the intent is to include electromagnetic waves.

I claim:

1. A combination of a multiple dilutor and a multiple probe colorimeter both temperature controlled by a circulating liquid for carrying out colorimetrical tests on batches of liquid samples and said multiple dilutor comprising of many modified syringes inclosed in a liquid tight enclosure with part of their tips protruding a few centimeters below the bottom of said liquid tight enclosure and the opposite end of the cylinder part of each modified syringe is anchored in the top part of said liquid tight enclosure in a manner that the plungers are controlled from the outside of said liquid tight enclosure and there is provision for temperature controlled liquid to enter, flow around said modified syringes, and leave through an outlet, the outer ends of said plungers are connected to a movable handle, stops control the amount or reagent, air-bubble, and liquid sample to be metered simultaneously, said multiple colorimeter comprising a light tight enclosure, near the bottom filtered electromagnetic waves are directed up through many lenses that are sealed in a horizontal plane into a second bottom wherein is a temperature controlled liquid bath, reaction tubes with opaque walls and optical bottoms are situated above each said lens in said temperature controlled liquid bath, a removeable cover has many probes with optical bottoms wherein each has an electromagnetic wave sensing device, said probes are attached to said removeable cover in a manner that each said probe enters each said reaction tube and said optical bottom of each said probe rests the same distance from each said optical bottom of said reaction tubes, the said tips of said multiple dilutor are so spaced they fit into each said reaction tube for emptying the test sample and reagent at the proper temperature simultaneously into said reaction tubes which are also at the proper temperature, a stirrer is attached to each said probe in a manner to allow simultaneous agitation by movement of said cover, said filtered electromagnetic waves pass through the liquid samples as they react and to said electromagnetic wave sensing devices which store an electrical current in a manner responsive to the electromagnetic wave absorbing characteristics of its corresponding liquid sample in an electrical storage device, by means of control switches said electrical currents are stored simultaneously at timed intervals in many said storage devices, the said electrical current in each said storage device is interpreted by use of an electrical measuring device.

2. The structure of claim 1 wherein said electromagnetic wave source and said electromagnetic wave sensing devices are exchanged in position.

3. The structure of claim 1 wherein said multiple dilutor has a second modified syringe smaller in size added to each said modified syringe with the plungers of said second modified syringes attached to a second movable handle independent of said movable handle, said second modified syringe tip is very short and sealed into said dilutor tip, thus said dilutor tip is a common tip for said modified syringe and said second modified syringe.

* * * * *